United States Patent [19]

Kotera et al.

[11] 4,111,979

[45] Sep. 5, 1978

[54] PROCESS FOR PRODUCING 8-AMINO-1-NAPHTHOL-3,6-DISULFONIC ACID

[75] Inventors: Norio Kotera, Amagasaki; Hiromichi Okabe, Hirakata; Hiroshi Korenaga, Toyonaka, all of Japan

[73] Assignee: Sumitomo Chemical Company, Limited, Osaka, Japan

[21] Appl. No.: 807,187

[22] Filed: Jun. 16, 1977

[30] Foreign Application Priority Data

Jun. 21, 1976 [JP] Japan ................................. 51-73723

[51] Int. Cl.$^2$ ........................................... C07C 143/30
[52] U.S. Cl. ..................................... 260/509; 260/508
[58] Field of Search ......................................... 260/509

[56] References Cited

U.S. PATENT DOCUMENTS

| 1,573,056 | 2/1926 | Gubelmann et al. | 260/509 |
| 1,670,406 | 5/1928 | Gubelmann et al. | 260/509 |
| 2,875,243 | 2/1959 | Roos et al. | 260/509 |

FOREIGN PATENT DOCUMENTS 190,114  3/1924  United Kingdom ..................... 260/509

Primary Examiner—Joseph E. Evans
Attorney, Agent, or Firm—Stevens, Davis, Miller & Mosher

[57] ABSTRACT

In a process for producing 8-amino-1-naphthol-3,6-disulfonic acid which comprises subjecting a 1-nitronaphthalene-3,6,8-trisulfonic acid reaction mixture to reduction, subjecting the resulting 1-naphthylamine-3,6,8-trisulfonic acid salt mixture to alkali fusion and subjecting the alkali fusion mixture to precipitation by mixing with an acid to obtain 8-amino-1-naphthol-3,6-disulfonic acid as a partial alkali metal salt, the amount of acids and bases used can be curtailed and the quality of the product can be improved by performing the precipitation by mixing said alkali fusion mixture with said 1-nitronaphthalene-3,6,8-trisulfonic acid reaction mixture, separating the precipitated partial alkali metal salt of 8-amino-1-naphthol-3,6-disulfonic acid by filtration, and using as a starting material for said reduction reaction the resulting filtrate containing 1-nitronaphthalene-3,6,8-trisulfonic acid and/or a salt thereof.

9 Claims, No Drawings

PROCESS FOR PRODUCING 8-AMINO-1-NAPHTHOL-3,6-DISULFONIC ACID

The present invention relates to a process for producing 8-amino-1-naphthol-3,6-disulfonic acid (hereinafter referred to as "H acid") as a partial alkali metal salt. More particularly, the invention pertains to a process for producing H acid which comprises subjecting a 1-nitronaphthalene-3,6,8-trisulfonic acid-containing mixture obtained by trisulfonation of naphthalene, followed by nitration (hereinafter referred to as "nitro mixture") to reduction, subjecting the resulting 1-naphthylamine-3,6,8-trisulfonic acid (hereinafter referred to as "Koch acid") salt mixture to alkali fusion, and subjecting the resulting alkali fusion mixture (hereinafter referred to as "fusion mass") to precipitation by mixing the fusion mass with an acid to obtain H acid as a partial alkali metal salt (the precipitation by mixing the fusion mass with an acid being hereinafter referred to as "acidification precipitation" for brevity), characterized in that the acidification precipitation is performed by mixing said fusion mass with said nitro mixture, the precipitated partial alkali metal salt of H acid is separated by filtration, and the resulting filtrate containing 1-nitronaphthalene-3,6,8-trisulfonic acid (hereinafter referred to as "nitrosulfonic acid") and/or a salt thereof is used as a starting material for said reduction reaction.

H acid has long been manufactured and used as an intermediate for the production of dyes and pigments, and is now still one of the most important intermediates of naphthalene series. The general process for the production of H acid comprises obtaining Koch acid from naphthalene by sulfonation, nitration and reduction and then subjecting the Koch acid to alkali fusion as shown by the formula,

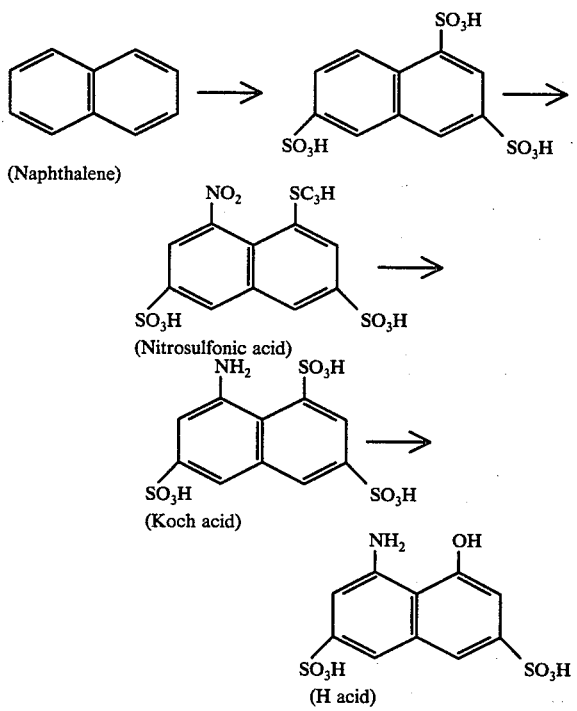

Problems in the process are that the overall yield of H acid from naphthalene is low and a large amount of acids and bases, etc. are required. For example, according to the process as described on pages 533 to 536 of Yutaka HOSODA, "Senryo Kagaku (Dye Chemistry)", the amount of caustic soda used for alkali fusion of 1 mole of Koch acid acid trisodium salt is 8.6 moles which corresponds to 4.3 times the theoretically required amount (2 moles). As a result, the amount of sulfuric acid required for obtaining H acid as its monosodium salt from the fusion mass reaches 5.8 moles for 1 mole of Koch acid. Also, the amount of all sulfuric acid used for trisulfonation of naphthalene in the first step is 7.2 moles per mole of naphthalene which corresponds to 2.4 times the theoretical amount (3 moles per mole of naphthalene). The nitro mixture obtained in the subsequent nitration step contains sulfuric acid as one component of a mixed acid as a nitrating agent and contains a large amount of sulfuric acid in addition to nitrosulfonic acid as a necessary component.

According to the present inventors' follow-up, the use of such an excess of auxiliary material (e.g. acids and bases) in these respective reaction steps is unavoidable to a certain extent. It has been found that it is almost impossible to curtail sharply the amounts of these auxiliary materials used without impairing the other advantages of the process although there is some room for improvement in the process. The use of an excess of auxiliary materials (for example, acids) in these reaction steps causes the use of a large amount of the other auxiliary materials (for example, bases) for neutralization in the subsequent steps. As a result, most of the cost of raw and processed materials for the manufacture of H acid is occupied by the cost of acids and bases. Also, a vast amount of waste acid or inorganic salt-containing drainage is produced and an economic burden for treating them is not negligible.

It is, therefore, the principal object of the present invention to avoid the difficulties heretofore encountered in the production of H acid from the nitro mixture.

It is a further object to provide a process for producing H acid which is not only inexpensive in operation but also produces a product of high quality.

Another object of the present invention is to provide an improved process for producing H acid.

These and other objects and advantages of the invention will be apparent from the following description of the invention.

As a result of the present inventors' extensive studies on curtailing the amount of acids and bases in the production of H acid, it has been found that H acid precipitates almost quantitatively in the form of a partial alkali metal salt, mainly as a mono alkali metal salt, and the nitrosulfonic acid in the nitro mixture remains almost completely in the solution while it is partly neutralized, if the fusion mass of Koch acid is subjected to the acidification precipitation using the nitro mixture.

Also, it has been found that 5-amino-2-naphthol-4,7-disulfonic acid (hereinafter referred to as "W acid") present in the fusion mass as a by-product can be separated from H acid by the acidification precipitation using the nitro mixture more effectively than a conventional acidification precipitation using an aqueous mineral acid solution.

According to the present invention, there is provided the improvement in a process for producing 8-amino-1-naphthol-3,6-disulfonic acid which comprises subjecting a 1-nitronaphthalene-3,6,8-trisulfonic acid reaction mixture obtained by trisulfonation of naphthalene, followed by nitration to reduction, subjecting the resulting 1-naphthylamine-3,6,8-trisulfonic acid salt mixture to alkali fusion, and subjecting the resulting alkali fusion mixture to precipitation by mixing with an acid to obtain 8-amino-1-naphthol-3,6-disulfonic acid as a partial alkali metal salt, characterized in that the precipitation is performed by mixing the said alkali fusion mixture with said 1-nitronaphthalene-3,6,8-trisulfonic acid reaction mixture, the precipitated partial alkali metal salt of 8-amino-1-naphthol-3,6-disulfonic acid is separated by filtration, and the resulting filtrate containing 1-nitronaphthalene-3,6,8-trisulfonic acid and/or a salt thereof is used as a starting material for said reduction reaction.

In the present invention, by mixing the fusion mass containing an excess of bases with the nitro mixture containing an excess of acids, the precipitation of H acid can be effected without adding a fresh acid. Moreover, the neutralization of the nitro mixture, which is necessary for the subsequent reduction reaction, is simultaneously effected, so that base burden can be remarkably curtailed.

Further, curtailment of the amounts of acids and bases used results in a decrease in the amount of inorganic salts formed in all the steps, a decrease in the amount of water for dissolving the salts, and further a drastic reduction of the amount of the whole drainage.

As the fusion mass used in the present invention, one wherein an alkali metal is sodium and/or potassium is suitable. Such a fusion mass can be easily obtained by selecting the kind of the starting Koch acid salt and/or the kind of a caustic alkali. The fusion mass usually contains sodium sulfite as a by-product, the remaining base and water, and further, as organic components, W acid and 1,8-dihydroxynaphthalene-3,6-disulfonic acid (hereinafter referred to as "chromotropic acid") as by-products in addition to H acid as a main component, in the form of alkali metal salts.

It is difficult to obviate the formation of these by-products completely under such fusion conditions as is practicable commercially and economically, although the amount of the by-products formed can be controlled to a certain degree by selecting the fusion conditions. The preferable composition of the fusion mass in the practice of the present invention is as follows:

In 100 parts by weight of a fusion mass,

|  | Parts by weight |
| --- | --- |
| H acid salt | 10 to 40 |
| W acid salt | 0.1 to 3 |
| Chromotropic acid salt | 0.1 to 3 |
| Sodium sulfite | 3 to 25 |
| Alkali component | 5 to 30 |
| Water | 30 to 60 |

However, the composition of the fusion mass is not restricted at all in the practice of the present invention.

The nitro mixture used for the acidification precipitation is usually produced from naphthalene by sulfonation and then nitration and may contain not only nitrosulfonic acid but also its isomers, nitric acid, etc. The rough composition of the nitro mixture is 20 to 70% by weight of nitrosulfonic acid containing isomers thereof and 30 to 80% by weight of sulfuric acid. These fusion mass and nitro mixture may be previously subjected to pre-treatments such as dilution, filtration, partial neutralization, etc.

The acidification precipitation is carried out at a pH of 2.5 or less, preferably 2.0 or less, and at a temperature of from room temperature to the boiling point of the fusion mass. The filtration temperature is suitably 85° C or lower, more preferably 30° to 60° C. The concentration of H acid in the acidification precipitation mixture is suitably about 2% by weight to about 25% by weight, the concentration of nitrosulfonic acid about 5% by weight to about 30% by weight, and the concentration of inorganic salts about 5% by weight to about 30% by weight. Preferable concentration ranges are affected by the compositions and quantitative relationship of the fusion mass and nitrosulfonic acid, but such conditions as H acid is almost completely precipitated and nitrosulfonic acid is almost quantitatively dissolved can be selected within the above-mentioned concentration ranges.

The partial alkali metal salt of H acid thus precipitated is separated by filtration and, if necessary, subjected to simple purification such as washing with water or dilute sulfuric acid to obtain a final product.

In a conventional acidification precipitation using an aqueous solution of a mineral acid such as sulfuric acid, hydrochloric acid, etc., contamination of H acid by the inorganic salts and by-products can be decreased to a certain extent. However, it is difficult to minimize the amount of W acid contained in the product since W acid is similar to H acid in properties. This is a technical difficulty in the manufacture of H acid. Also, it is known that contamination of H acid by W acid has a great influence upon the quality of H acid when used in, for example, the manufacture of dyes. Therefore, contamination of H acid by W acid is utilized as one criterion showing the quality of H acid. Also, any additional purification step for removing W acid causes a decrease in the yield of H acid and will thereby be an economically disadvantageous factor.

According to the process of the present invention, however, highly pure H acid substantially free from W acid can be obtained easily. Thus, not only curtailment of the amount of acids and bases used but also the improvement in the quality of the product can be attained according to the process of the present invention.

The operation can be carried out by either batch type method or continuous method. The filtrate containing the nitrosulfonic acid dissolved therein can be used as a starting material in the subsequent reduction step as it is. Examples of a preferable form as the starting material in reduction step are (1) the filtrate as it is or after its concentration or pH was adjusted, (2) the nitrosulfonic acid salts separated by salting-out and filtration, and (3) the solution freed from sulfates after neutralization with lime and filtration. Any of these examples can be easily practiced by those skilled in the art. Reduction method can be selected from known methods such as reduction with a metal or a metal powder, catalytic hydrogenation, etc.

In order for only the curtailment of the amounts of acids and bases, it is considered to use the sulfonation mixture before the nitration to obtain the nitrosulfonic acid, or the acidic reduction mixture containing Koch acid, for the acidification precipitation. If said sulfonation mixture is used, however, there is a problem in suitability of the filtrate containing naphthalenetrisulfonic acid salts for the nitration. Also, if said acidic reduction mixture is used, Koch acid precipitates together with H acid. Thus, such precipitation is not practical.

The present invention is further illustrated by the following examples, in which all parts and % are expressed by weight unless otherwise indicated. Of course, this invention shall not be limited to the examples.

EXAMPLE 1

According to a usual method naphthalene was sulfonated and then nitrated. The reaction mixture was added to water and air is then blown thereinto to remove $NO_x$ gas. Thus, nitro mixture containing 23.6% of nitrosulfonic acid, 5.5% of nitrosulfonic acid isomers and 33.3% of sulfuric acid was obtained.

To 5,800 parts of a wet cake containing 2,175 parts of Koch acid trisodium salt was added 3,600 parts of 48% caustic soda and the mixture was maintained at 180° to 185° C for 3 hours. After cooling, the mixture was diluted with 5,000 parts of water and added gradually to 10,000 parts of the nitro mixture obtained above. The mixture was heated at the boiling point for 30 minutes. The pH of the mixture was less than 1. After cooling to 40° C, the mixture was filtered. The filter cake was washed with water and then dried to obtain 1,354 parts (as pure salt) of H acid monosodium salt. The content of nitrosulfonic acid in the cake was presumed to be substantially zero from the fact that there was no difference between diazo value and diazo value after reduction within the range of the experimental error of the analytical method used. Also, it was found by high speed liquid chromatography that the content of W acid in the cake was less than the detection limit of the analytical method.

The filtrate was reduced with 1,500 parts of scrap iron, neutralized and then precipitated by the addition of an acid to obtain 5,800 parts of a wet cake containing 2,175 parts of Koch acid trisodium salt.

EXAMPLE 2

To 5,185 parts of a slurry containing 2,175 parts of Koch acid trisodium salt was added 2,680 parts of a 50% caustic potash solution. The mixture was heated at 195° C for 2 hours. After cooling, the mixture was diluted with 5,000 parts of water and then added to 10,000 parts of the same nitro mixture as one used in Example 1. The pH of the resulting mixture was less than 1. The mixture was heated at 85° to 90° C for 30 minutes, cooled gradually and then filtered at 35° to 40° C. The filter cake was washed with water and dried to obtain 1,418 parts (as pure salt) of H acid monopotassium salt.

Neither nitrosulfonic acid nor W acid was detected in the cake by the same analytical methods as those used in Example 1.

After neutralization with lime, the filtrate was freed from sulfates, reduced with iron powder and hydrochloric acid, sodated and then precipitated by the addition of an acid to obtain 5,600 parts of a wet cake containing 2,368 parts of Koch acid dipotassium salt.

EXAMPLE 3

To a precipitation tank was supplied a nitro mixture containing 26.1% of sulfuric acid, 27.0% of nitrosulfonic acid and 5.8% of nitrosulfonic acid isomers, as produced in sulfonation step excluding an excess of sulfuric acid, at a rate of 620 parts per hour. On the one hand, a fusion mass containing 23.2% of H acid trisodium salt, 18.7% of caustic soda and 7.6% of sodium sulfite was supplied to the same precipitation tank at a rate of 535 parts per hour. The precipitation tank was kept at a pH of less than 1. The sulfur dioxide gas generated was continuously exhausted. The precipitated mixed liquid was cooled to 40° C by way of a two-stage continuous crystallization tank, and the separated crystals were continuously filtered. The filter cake was washed with water and recovered as a paste containing 35% of H acid at a rate of 400 parts per hour. 248 Parts per hour of the washing was supplied to the precipitation tank. The filtrate was neutralized to a pH of 6. The neutralized filtrate becomes a starting material for the production of Koch acid by catalytic hydrogeneration in the presence of a palladium-on-carbon catalyst. The Koch acid sodium salt obtained therefrom was supplied to fusion step and converted into the above-mentioned fusion mass, which was in turn sent to the precipitation tank. The above-mentioned process was conducted repeatedly until the reaction system came to have a constant composition. No influence was observed on the quality of the product H acid.

Comparative Example

To 5,800 parts of a wet cake containing 2,175 parts of Koch acid trisodium salt was added 3,600 parts of 48% caustic soda. The resulting mixture was kept at 180° to 185° C for 3 hours. This fusion mass was cooled to 80° C, and then added gradually to an aqueous sulfuric acid solution consisting of 13,700 parts of water and 2,800 parts of 98% sulfuric acid. The resulting mixture was heated at the boiling point for 30 minutes. The pH of the mixture was less than 1. The mixture was cooled to 40° C and then filtered. The filter cake was washed with water and dried to obtain 1,350 parts (as pure salt) of H acid monosodium salt. However, the H acid cake contained 2.5% of W acid based on the weight of H acid.

What is claimed is:

1. In the process for producing 8-amino-1-naphthol-3,6-disulfonic acid from naphthalene by trisulfonation, nitration, reduction, alkali fusion and acidification precipitation, the improvement comprising acidifying the alkali fusion mixture with the nitration reaction mixture to precipitate the partial alkali metal salt of 8-amino-1-naphthol-3,6-disulfonic acid which is separated by filtration, and using the resulting filtrate containing 1-nitronaphthalene-3,6,8-trisulfonic acid and/or salt as the starting material for the reduction reaction.

2. A process according to claim 1, wherein the alkali fusion mixture is previously treated by dilution, filtration or partial neutralization before the precipitation.

3. A process according to claim 1, wherein the nitration reaction mixture is previously treated by dilution, filtration of partial neutralization before it is used in the precipitation.

4. A process according to claim 1, wherein the precipitation is performed at a pH of 2.5 or less.

5. A process according to claim 4, wherein the precipitation is performed at a pH of 2.0 or less.

6. A process according to claim 1, wherein the precipitation is performed at a temperature of from room temperature to the boiling point of the alkali fusion mixture.

7. A process according to claim 1, wherein the filtration is conducted at a temperature of 85° C or less.

8. A process according to claim 7, wherein the filtration is conducted at a temperature of 30° to 60° C.

9. A process according to claim 1, wherein the resulting mixture of the alkali fusion mixture with the nitration reaction mixture in the precipitation step contains about 2 to about 25% by weight of 8-amino-1-naphthol-3,6-disulfonic acid, about 5 to about 30% by weight of 1-nitronaphthalene-3,6,8-trisulfonic acid and about 5 to about 30% by weight of inorganic salts.

* * * * *